United States Patent
Nomura et al.

(10) Patent No.: US 6,531,508 B1
(45) Date of Patent: Mar. 11, 2003

(54) ANTIBACTERIAL MEDICINAL COMPOSITIONS

(75) Inventors: Masaaki Nomura, Gunma (JP); Osamu Sugita, Gunma (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/856,094

(22) PCT Filed: Sep. 18, 2000

(86) PCT No.: PCT/JP00/06346

§ 371 (c)(1),
(2), (4) Date: Jun. 26, 2001

(87) PCT Pub. No.: WO01/21175

PCT Pub. Date: Mar. 29, 2001

(30) Foreign Application Priority Data

Sep. 17, 1999 (JP) .......................................... 11-264637

(51) Int. Cl.⁷ ............................................. A61K 31/195
(52) U.S. Cl. ....................................... 514/561; 424/489
(58) Field of Search ........................... 514/561; 424/489

(56) References Cited

FOREIGN PATENT DOCUMENTS

| EP | 121502 | 10/1984 |
|---|---|---|
| EP | 0 121 502 | 10/1984 |
| EP | 399781 | 11/1990 |
| EP | 0 497 353 A2 | 8/1992 |
| EP | 497353 | 8/1992 |
| GB | 909 365 A | 10/1962 |
| GB | 1061426 | 3/1967 |
| JP | 7-69887 | 3/1995 |
| JP | 8-12675 | 1/1996 |
| WO | WO99/36098 | 7/1999 |

OTHER PUBLICATIONS

Database WPI, Section Ch, Week 199937; Derwent Publications Ltd., London, GB; AN 1999–444328, XP002198932 & WO 99 36098 A (Suntory Ltd.), Jul. 22, 1999, abstract, & EP 0 966 974 A (Suntory Ltd) Dec. 29, 1999.

Suzuka et al, "Effect of Salicylate and Disodium EDTA on the Rat Intestinal Absorption of Cefmetazole", Chemical and Pharmaceutical Bulletin (Tokyo), vol. 33, No. 10, 1985, pp. 4600–4605, XP001069054.

Prous et al, "SUN–5555: Penem." Drugs of the Future, vol. 18, No. 6, 1993, pp. 525–528, XP001070488.

Primary Examiner—Dwayne C. Jones
Assistant Examiner—C. Delacroix-Muirheid
(74) Attorney, Agent, or Firm—Nixon & Vanderhye P.C.

(57) ABSTRACT

A technique for realizing the wide application of penem compounds as pharmaceutical antibacterial compositions is disclosed. The composition contains a penem compound as an active ingredient characterized in that it contains an α,ω-diamineacetate compound.

8 Claims, No Drawings

ANTIBACTERIAL MEDICINAL COMPOSITIONS

FIELD OF THE INVENTION

The present invention relates to pharmaceutical antibacterial compositions containing a penem antibiotic as an active ingredient, which are stable and show good gastrointestinal absorption.

PRIOR ART

Penem compounds are non-natural β-lactam compounds the design of which is based on the concept of fusing the structures of penicillin and cephalosporin (for example, see Woodward, R. B., In Recent Advances in the Chemistry of β-Lactam Antibiotics, Elks, J., Ed., The Chemical Society, London, 1977, Spec. No. 28, pp. 167–180; Japanese Patent Public Disclosure(Kokai) Nos. 207387/86, 162694/88, 222486/85 and 119486/79). They are a novel type of antibiotic having both the wide antibacterial spectrum and high safety of penicillin and cephem antibiotics belonging to β-lactam antibiotics, as well as the potent antibacterial activity and high β-lactamase stability of carbapenem antibiotics. Sodium (+)-(5R,6S)-6-[(R)-1-hydroxyethyl]-7-oxo-3-[(R)-2-tetrahydrofuryl]-4-thia-1-azabicyclo[3.2.0]hept-2-ene-2-carboxylate 5/2 hydrate (faropenem sodium, hereinafter referred to as compound 1) is currently used as an oral drug for various infectious diseases and is reported to show potent antibacterial activity against not only methicillin-sensitive *Staphylococcus aureus* (MSSA), *Streptococcus pyogenes* and *Streptococcus pneumoniae* but also gram-positive bacteria for which conventional β-lactam drugs have proved ineffective such as penicillin-resistant pneumococci (PRSP), oral staphylococci and enterococci, also showing a wide antibacterial spectrum covering gram-negative bacteria such as *Haemophilus influenzae* and anaerobic bacteria such as the genus Bacteroides, which activity is due to its novel skeleton penem ring ((Kagaku Ryoho no Ryoiki The Field of Chemotherapy), Vol. 13, No. 10, pp. 74–80, 1997). This compound is also reported to have potent antibacterial activity against pathogenic bacteria of periodontis such as *Porphyromonas gingivalis* (CHEMOTHERAPY, Vol. 42, S-1, pp. 38–50, 1994) as well as potent antibacterial activity against bacterial strains from dental infectious diseases which have recently become more and more resistant (Journal of Japan Chemotherapy Society, Vol. 45, No. 11, pp. 965–971, 1997).

However, penem compounds are chemically unstable materials susceptible to hydrolysis, oxidation, photoisomerization and the like, in much the same way as other β-lactam compounds.

Moreover, water-soluble β-lactam compounds are known to show poor gastrointestinal absorption as compared with fat-soluble compounds (Akinobu Otsuka et al., Pharmaceutics, Revised 2nd Edition., Nankodo). Such drugs tend not to produce a reliable therapeutic effect, and, antibacterial compounds such as penem compounds also have a tendency to affect the flora of enteric bacteria thereby inducing loose stools or diarrhea.

Thus, the application range, administration route and dosage form of penem compounds have been limited due to their instability and poor gastrointestinal absorption.

Syrup is a dosage form which is easy to swallow even for seniors and children. It is a dosage form with excellent characteristics which masks a bitter or unpleasant taste of drugs with the sweetening effect and consistency of sugars and various flavoring agents, and improves palatability with suitable colorants giving a pleasant color and the like. Dry syrups to be dissolved or suspended before use have been studied in the case of active ingredients unstable in water. Dry syrups are dissolved or suspended before use in an aqueous liquid such as water, juice or milk as a solvent.

Several dry syrup formulations have been developed for antibiotics which are generally unstable in water. Examples include macrolide antibiotic formulations such as josamycin propionate (Josamy Dry Syrup® from Yamanouchi Pharmaceutical) or erythromycin ethylsuccinate (Erythrocin Dry Syrup® from Dainippon Pharmaceutical) and cephem antibiotic formulations such as cefpodoxime proxetil (Banan Dry Syrup® from Sankyo), all of which are used as suspensions in water added before use.

When dry syrups are used as suspensions in hospitals, for example, they are often combined with water and kept to stand before they are taken by inpatients. Also at home, dry syrups are mostly taken in divided portions after being dispersed or dissolved in water. In these cases, suspensions are allowed to stand and insoluble ingredients precipitate to affect homogeneity of active ingredients and therefore the dosage regimen is not faithfully followed.

From the viewpoint of palatability, patients' rejection of medication must be avoided, especially in the case of children having a disease. However, suspensions are not only disliked for their texture but are also responsible for oral or digestive discomfort due to the presence of insoluble ingredients, leading to children to reject second and subsequent doses. In seniors, insoluble ingredients may enter the gaps between false teeth to cause pain. This decreases patient compliance and therefore the dosage regimen is not faithfully followed.

It is known that α,ω-diamineacetate compounds form complexes with a metal ion such as copper or iron, and thus inhibit decomposition reactions which are catalyzed by heavy metals, making them suitable for use as stabilizers against components susceptible to such reactions such as fats and the active ingredients of some drugs.

Among α,ω-diamineacetate compounds, disodium ethylenediaminetetraacetate is thought to increase penetration into intercellular spaces by forming a complex with a calcium ion thereby retaining the structure of intracellular spaces of gastrointestinal mucosa (Ryuji Iga et al., Recent Advances in Biopharmacy, 1994, Yakujinippo).

As described above, there are demands for widely applying penem compounds having high safety and potent antibacterial activity as pharmaceutical antibacterial compositions, but the actual demands have not been sufficiently satisfied because any techniques for formulating them into various dosage forms such as oral formulations or solutions have not been developed. For children and seniors, safe and effective antibacterial compositions which ensure proper patient compliance and require only an easy-to-follow dosage regimen would be especially desirable.

SUMMARY OF THE INVENTION

As a result of careful studies of formulation techniques focusing on stability in aqueous solution and gastrointestinal absorption of penem compounds with a view to developing a technique for administering penem compounds as pharmaceutical antibacterial compositions, the present invention has been accomplished. Specifically, the inventors have found that penem compounds are stable in solvents comprising water and, more surprisingly, improved gastrointestinal absorption can be imparted to these compounds by incorporating an α,ω-diamineacetate compound into the composition.

Accordingly, the present invention provides pharmaceutical antibacterial compositions containing a penem compound as an active ingredient which can be formulated into various dosage forms such as oral formulations and solutions, particularly syrups, especially dry syrups which allow highly water-soluble penem compounds to be administered to seniors and children as clear aqueous solutions with good compliance.

Compositions of the present invention are pharmaceutical antibacterial compositions containing a penem compound as an active ingredient, $\alpha,\omega$-diamineacetate compound and optionally other additives.

DETAILED DESCRIPTION OF THE INVENTION

Penem compounds used in the present invention are not specifically limited so far as they have antibacterial activity and safety including the absence of immunogenicity and oral toxicity and are pharmaceutically acceptable. These may be free carboxylic acids or pharmaceutically acceptable salts thereof with alkali metals or alkali earth metals such as sodium, potassium, calcium or magnesium, or amino acids such as lysine, or ammonium, and may also be used as solvates such as hydrates. When pharmaceutical compositions of the present invention are required to be water-soluble, penem compounds as active ingredients can be appropriately selected, taking into account their water solubility.

Penem compounds used in the present invention include faropenem sodium mentioned above (compound 1), which may optionally be substituted at 3-position by 1,4-dioxane-2-yl, ethylsulfanyl, 3-tetrahydrofurylmethyl, methoxymethyl, ((aminocarbonyl)oxy)methyl, (4R)-pyrrolidine-2-thione-4-ylthio and other groups.

The amount of active ingredients to be contained in the composition of the invention can be determined appropriately depending on the nature of the active ingredient, the disease to be treated or other factors. When compound 1 is used, it is incorporated at about 10–90% by weight for tablets, about 50–99.9% by weight as solids for injections and about 2–20% by weight for dry syrups in terms of the free anhydride relative to the total composition.

$\alpha,\omega$-Diamineacetate compounds are linear hydrocarbons having an aminoacetate group at each end. Linear hydrocarbons of $\alpha,\omega$-diamineacetate compounds used in the present invention may contain an aminoacetate group(s) in the chain. The size the hydrocarbon chain is not limited, but preferably ethylene is desirable.

Examples of $\alpha,\omega$-diamineacetate compounds include polyaminocarboxylic acid chelating agents such as ethylenediaminetetraacetic acid, hydroxyethylethylenediaminetriacetic acid, dihydroxyethylethylenediaminediacetic acid, 1,3-propanediaminetetraacetic acid, diethylenetriaminepentaacetic acid, triethylenetetraminehexaacetic acid and salts thereof. They may be used as solvates such as hydrates. Especially, ethylenediaminetetraacetic acid and salts thereof are preferably used in respect of safety, specifically calcium ethylenediaminetetraacetate, disodium calcium ethylenediaminetetraacetate, sodium ethylenediaminetetraacetate, disodium ethylenediaminetetraacetate, tetrasodium ethylenediaminetetraacetate, tetrasodium ethylenediaminetetraacetate tetrahydrate. The present invention is not limited to these examples, but one or more $\alpha,\omega$-diamineacetate compounds can be appropriately selected and used.

The amount of $\alpha,\omega$-diamineadetate compounds to be added in compositions of the present invention depends on the nature of the compound or the dosage form of the composition, but can be determined by evaluating the stability in solvents comprising water and the gastrointestinal absorption of the penem compound. Normally, they are contained at about 0.1–100%, preferably about 0.1–20% relative to active ingredients as free anhydrides.

In the present invention, stability of penem compounds is improved. Therefore, pharmaceutical antibacterial compositions of the present invention can be used as formulations to be administered in the state where they are dissolved or suspended in a solvent comprising water, i.e. (1) solutions or suspensions in solvents comprising water or (2) formulations to be dissolved or suspended before use. These formulations include injections, solutions, syrups, ophthalmic solutions, suspensions, emulsions, aerosols, elixirs, capsules containing a solution or suspension, liniments, lemonades or lotions. For example, injections may be either solutions or formulations to be dissolved or suspended before use. As used herein, formulations to be dissolved or suspended before use mean formulations which are shipped in a solid form but dissolved or suspended between opening and application. Normally, they are dissolved or suspended immediately before application.

Various dosage forms of formulations to be administered in the state where they are dissolved or suspended in a solvent comprising water can be prepared by incorporating an active ingredient, an $\alpha,\omega$-diamineacetate compound and other additives via the routine process for each dosage form. For example, injections may contain as other additives (1) isotonizing agents such as sodium chloride, D-mannitol, D-sorbitol, (2) pH modifiers such as hydrochloric acid, citric acid, sodium hydroxide, (3) buffers such as sodium citrate, phosphoric acid, sodium phosphate, potassium phosphate, sodium acetate, boric acid, (4) soothing agents such as procaine hydrochloride and surfactants. The amounts of these additives can be appropriately determined depending on the pharmaceutical characteristics desired or other factors.

Pharmaceutical antibacterial compositions of the present invention are useful not only as the formulations described above but also as any other formulations prepared by processes including the step of bringing active ingredients into contact with water, e.g. the step of adding active ingredients dissolved in water because stability of penem compounds is improved in the present invention. Examples of such other formulations include tablets, capsules, pills, granules, fine granules and powders prepared via such an operation as fluidized bed granulation, agitating granulation, kneading granulation or coating.

In the present invention, pharmaceutical antibacterial compositions having good gastrointestinal absorption can be obtained by incorporating an $\alpha,\omega$-diamineacetate compound. Thus, pharmaceutical antibacterial compositions of the present invention are useful as oral formulations such as tablets, capsules, solutions, syrups, pills, granules, fine granules, powders, troches, aerosols, elixirs, lemonades, etc.

These formulations can be prepared by incorporating an active ingredient, an $\alpha,\omega$-diamineacetate compound and other additives via the routine process.for each dosage form. For example, tablets may contain (1) excipients such as lactose, starches or microcrystalline celluloses, (2) binders such as hydroxypropyldellulose or polyvinylpyrrolidone, (3) disintegrating agents such as starches or sodium carboxymethylcellulose, (4) lubricants such as magnesium stearate or talc, (5) coating bases such as hydroxypropylmethylcellulose or Eudragit, as well as plasticizers and colorants. The amounts of these additives can be appropriately determined depending on the pharmaceutical characteristics desired or other factors.

Pharmaceutical antibacterial compositions of the present invention are useful as (1) oral formulations dissolved or suspended in water and (2) oral formulations to be dissolved or suspended before use, specifically solutions, syrups and dry syrups because the stability in the state where they are dissolved or suspended in a solvent comprising water and the gastrointestinal absorption of penem compounds are improved in the present invention.

Dry syrups means syrups to be dissolved or suspended before use, but the present invention also preferably encompasses similar powdery oral formulations such as granules, fine granules or powders containing a high ratio of sucrose and substantially suitable to be dissolved or suspended before use as embodiments of the present invention.

Dry syrups containing active ingredients to be homogeneously dissolved in water are one of the preferred embodiments of the present invention.

As used herein, dry syrups to be dissolved in water mean those which become clear and leave no trace of precipitated ingredients when mixed with an appropriate amount of water. Generally, the amount of water in which dry syrups are dissolved or suspended is determined taking into account (1) the influence of the concentration on the stability of the active ingredient, (2) ease of handling in the medical field, and (3) palatability for patients. For example, Josamy Dry Syrup (Yamanouchi Pharmaceutical) and Erythrocin Dry Syrup W (Dainippon Pharmaceutical) among commercially available dry syrups are shown to prepare suspensions at concentrations of 30, 40 and 100 mg (potency)/mL in the package inserts. Pharmaceutical compositions of the present invention can be used as dry syrups to be homogeneously dissolved in water within a wide concentration range of active ingredients, specifically at a concentration of 5–200 mg (potency)/mL, for example, 40 mg (potency)/mL, because the stability in solution or suspension in aqueous solvents and the gastrointestinal absorption of penem compounds are improved in the present invention. This is an especially preferred embodiment for faithfully following the dosage regimen and improving compliance in seniors and children.

Dry syrups can be prepared by incorporating an active ingredient, an α,ω-diamineacetate compound and other additives via the routine process for each dosage form. Such other additives include (1) excipients such as sucrose, lactose, fructose, mannitol, dextrose, (2) binders such as hydroxypropylcellulose or polyvinylpyrrolidone, (3) disintegrating agents such as starches, (4) plasticizers such as Macrogols, polyethylene glycol and triethyl citrate, (5) corrigents such as aspartame and citrate, (6) coating bases such as hydroxypropylmethylcellulose or Eudragit, as well as flavoring agents and colorants. The amounts of these additives can be determined as required depending on the desired pharmaceutical characteristics or other factors.

Formulations prepared are packaged in the form suitable for each dosage form, such as bottling, divided powder, press through packaging, ampoules, vials. The dose of thus obtained formulations is typically 50–1500 mg (potency), preferably about 100–1000 mg (potency) daily per adult (60 kg) depending on the route of administration, the disease to be treated, the condition of the disease, the age and other factors. For children, the dose can be calculated on the basis of body weight.

EXAMPLES

The following examples further illustrate the present invention without, however, limiting the scope of the invention thereto.

Example 1

Evaluation of the Stability of Compound 1 in the Solid State

The effect of disodium ethylenediaminetetraacetate on the stability of compound 1 in the solid state was evaluated. A glass bottle containing a mixed powder or a compression molding having the composition shown in Table 1 was tightly sealed in the absence or presence of a desiccant and stored at 60° C. for 7 days to observe the appearance. None of the compositions showed any change in appearance (Table 1). Therefore, disodium ethylenediaminetetraacetate was incorporated into compositions of various dosage forms in the following examples.

TABLE 1

| Sample No. | 1–1 | 1–2 | 1–3 | 1–4 |
|---|---|---|---|---|
| Composition (weight in mg per tablet) | | | | |
| Faropenem sodium | 247 | 247 | 247 | 247 |
| Disodium ethylenediaminetetraacetate | — | 40 | — | 40 |
| Solid form | Mixed powder | Mixed powder | Compression molding | Compression molding |
| Stability test results | | | | |
| Desiccant | No | No | Yes | Yes |
| Initial appearance | White powder | White powder | White compression molding | White compression molding |
| Appearance after storage at 60° C./7 days | White powder | White powder | White compression molding | White compression molding |

Example 2

Evaluation of the Stability of a Compression Molding (Tablet) Containing Compound 1

The effect of disodium ethylenediaminetetraacetate on the stability of a compression molding (tablet) containing compound 1 in the solid state was evaluated. A glass bottle containing tablets having the composition shown in Table 2 prepared by the process described later (Preparation example 2 of tablet of Example 6) was tightly sealed in the absence of a desiccant and stored at 40° C. for one month to observe the appearance and determine the content of compound 1.

The content of compound 1 in tablets was determined by high-performance liquid chromatography as follows. A stainless steel high-performance liquid chromatography column packed with octadecylsilyl silica gel was used. The column temperature was 40° C. The mobile phase consisted of a binder of 870 mL of a solution containing 45 mM potassium dihydrogenphosphate, 5 mM sodium monohydrogenphosphate and 5 mM tetra-n-butylammonium bromide and 130 mL of acetonitrile. The flow rate was controlled to adjust the retention time of compound 1 to 11 min. For detection, a UV absorption spectrometer was used at a wavelength of 305 nm. The content of compound 1 was determined by the same method in Example 3 and 4 below.

Neither tablet showed any change in appearance, and the residual content of compound 1 was comparable irrespective of the presence or absence of disodium ethylenediaminetetraacetate (Table 2).

TABLE 2

| Sample No. | | 2–1 | 2–2 |
|---|---|---|---|
| Composition (weight in mg per tablet) | | | |
| Faropenem sodium | | 247 | 247 |
| Microcrystalline cellulose | | 20 | 20 |
| Hydroxypropylcellulose | | 9 | 9 |
| Magnesium stearate | | 4 | 4 |
| Glutathione | | 40 | 40 |
| Disodium ethylenediaminetetraacetate | | — | 10 |
| Solid form | | Compression molding | Compression molding |
| Stability test results | | | |
| Desiccant | | No | No |
| Initial appearance | | White tablet | White tablet |
| Storage at 40° C./ 1 month | Appearance | White tablet | White tablet |
| | Potency retention (%) | 95.2 | 94.9 |

Example 3

Evaluation of the Stability of Compound 1 in Aqueous Solution

The effect of disodium ethylenediaminetetraacetate on the stability of compound 1 in aqueous solution was evaluated. A glass bottle containing 5 mL of an aqueous solution having the composition shown in Table 3 containing 49.4 mg/mL (40.0 mg (potency)/mL) of compound 1 was tightly sealed and stored at room temperature for 7 days to observe the appearance and determine the content of compound 1.

As a result, the presence of disodium ethylenediaminetetraacetate had the effect of resisting change in appearance and loss of the residual content of compound 1 at concentrations of both 0.4 mg/mL and 2 mg/mL as compared with the control (without disodium ethylenediaminetetraacetate) (Table 3).

TABLE 3

| Sample No. | | 3–1 | 3–2 | 3–3 |
|---|---|---|---|---|
| Composition (mg/mL) | | | | |
| Faropenem sodium | | 49.4 | 49.4 | 49.4 |
| Disodium ethylenediaminetetraacetate | | — | 0.4 | 2 |
| Stability test results | | | | |
| Initial appearance | | Colorless clear | Colorless clear | Colorless clear |
| Storage at RT/7 days | Appearance | Light yellow clear | Pale yellow clear | Pale yellow clear |
| | Potency retention (%) | 90.5 | 92.1 | 92.4 |

Example 4

Evaluation of the Stability of Compound 1 in Suspension

The effect of disodium ethylenediaminetetraacetate on the stability of compound 1 in suspension was evaluated. A glass bottle containing 5 mL of a suspension having the composition shown in Table 4 containing 49.4 mg/mL of compound 1 in the presence of water-insoluble magnesium aluminometasilicate was tightly sealed and stored at 25° C. for 7 days to observe the appearance and determine the content of compound 1.

All the compositions were initially white suspensions after being combined with water. This is because magnesium aluminometasilicate is water-insoluble. After storage, the presence of disodium ethylenediaminetetraacetate had the effect of resisting change in appearance and loss of the residual content of compound 1 at any concentration of 0.4 mg/mL, 2 mg/mL or 4 mg/mL as compared with the control (without disodium ethylenediaminetetraacetate) (Table 4).

TABLE 4

| Sample No. | | 4–1 | 4–2 | 4–3 | 4–4 |
|---|---|---|---|---|---|
| Composition (mg/mL) | | | | | |
| Faropenem sodium | | 49.4 | 49.4 | 49.4 | 49.4 |
| Sucrose | | 240 | 240 | 240 | 240 |
| D-mannitol | | 120 | 120 | 120 | 120 |
| Magnesium aluminometasilicate | | 4 | 4 | 4 | 4 |
| Disodium ethylenediaminetetra-acetate | | — | 0.4 | 2 | 4 |
| Stability test results | | | | | |
| Initial appearance | | White suspension | White suspension | White suspension | White suspension |
| Storage at 25° C./ 7 days | Appearance | Yellow suspension | Pale greenish yellow suspension | Pale greenish yellow suspension | Pale greenish yellow suspension |
| | Potency retention (%) | 90.7 | 93.2 | 98.2 | 96.3 |

Examples 3 and 4 showed that disodium ethylenediaminetetraacetate improves the stability of compound 1 in aqueous solution or suspension.

Example 5

Improvement of Gastrointestinal Absorption of Compound 1

Seven-week old male Sprague-Dawley rats orally received 70.5 mg/kg (57.1 mg (potency)/kg) of compound 1 and 57.1 mg/kg of disodium ethylenediaminetetraacetate. Controls orally received 70.5 mg/kg of compound 1 alone. At 0.1–10 hours after administration, blood was collected. The concentration of compound 1 as free acid in plasma was determined by high-performance liquid chromatography. For determination, plasma was used after pretreatment. That is, 0.2 mL of plasma was stirred with 0.2 mL of acetonitrile and then centrifuged at 4° C., 12000 rpm for 15 min. Two hundreds µL of this supernatant was diluted in 800 µL of 10 mM phosphate buffer, and 200 µL of this dilution was applied on a high-performance liquid chromatography column. The chromatography conditions were as follows. A stainless steel high-performance liquid chromatographic column packed with octadecylsilyl silica gel was used. The column temperature was room temperature. The mobile phase consisted of a binder containing 680 mL of a 20 mM aqueous sodium dihydrogenphosphate solution adjusted at pH 2 with phosphoric acid and 320 mL of acetonitrile. The flow rate was controlled at 1 mL/min. For detection, a UV absorption spectrometer was used at a wavelength of 318 nm.

The results of analysis showed that the area under the plasma level-time curve (AUC) was approximately doubled in the group coadministered with disodium ethylenediaminetetraacetate as compared with the control group, demonstrating that disodium ethylenediaminetetraacetate has the excellent effect of improving gastrointestinal absorption of compound 1 (Table 5).

TABLE 5

|  | AUC ($\mu$g · hr/mL) |
|---|---|
| Control group | 12.6 ± 5.7 |
| Disodium ethylenediaminetetraacetate group | 24.8 ± 9.3 |

Example 6

Preparation Examples of Formulations

Preparation examples of formulations in various dosage forms containing compound 1 as an active ingredient together with an $\alpha,\omega$-diamineacetate compound are shown below.

Preparation example 1 of tablet

| Ingredients | Weight per tablet |
|---|---|
| Compound 1 | 247 mg |
| Corn starch | 20 mg |
| Hydroxypropylcellulose | 9 mg |
| Magnesium stearate | 4 mg |
| Disodium ethylenediaminetetraacetate | 10 mg |

Tablets each having the composition above were prepared as follows. All the components except for magnesium stearate were wet-granulated and then mixed with magnesium stearate. This mixture was compressed using a tablet machine to give a desired weight of tablets.

Preparation example 2 of tablet

| Ingredients | Weight per tablet |
|---|---|
| Compound 1 | 247 mg |
| Microcrystalline cellulose | 20 mg |
| Hydroxypropylcellulose | 9 mg |
| Magnesium stearate | 4 mg |
| Glutathione | 40 mg |
| Disodium ethylenediaminetetraacetate | 10 mg |

Tablets each having the composition above were prepared as follows. All the components except for magnesium stearate were wet-granulated and then mixed with magnesium stearate. This mixture was compressed using a tablet machine to give a desired weight of tablets.

Preparation example of injection

| Ingredients | Weight per vial |
|---|---|
| Compound 1 | 11.235 g |
| Disodium ethylenediaminetetraacetate | 0.012 g |

A lyophilized injection having the composition above per vial was prepared as follows. Compound 1 and disodium ethylenediaminetetraacetate were dissolved in water for injection in an amount equivalent to 9.8 g/vial. This solution was aseptically filtered through a filter of 0.22 $\mu$m to give a formulated solution to be lyophilized. This solution was aseptically packed in vials. An autoclave-sterilized rubber stopper was aseptically filled halfway into each vial. This vial was lyophilized in a lyophilization room. After confirming that the vial has been dried, the rubber stopper was completely fitted into the vial in the same room full of nitrogen gas. The vial was removed from the room to give a desired lyophilized injection.

When 10 mL of water for injection was added to the resulting lyophilized injection, the injection rap idly dissolved in it to give a clear solution.

Preparation example 1 of dry syrup

| Ingredients | Weight: mg/g |
|---|---|
| Compound 1 | 123.5 |
| Sucrose | 865.0 |
| Polyethylene glycol | 10.0 |
| Colorant Yellow No. 5 | 0.5 |
| Disodium ethylenediaminetetraacetate | 1.0 |
| Orange essence | trace |

A dry syrup having the composition above was prepared as follows. Compound 1, sucrose, polyethylene glycol and disodium ethylenediaminetetraacetate were mixed in an agitating granulator. This mixture was granulated by agitation while spraying it with a solution of Yellow No. 5 in water. These granules wore dried in a fluidized bed granulator and then sprayed with orange essence. The granules were further dried in the same apparatus and then removed and screened through a 30-mesh sieve to give a desired dry syrup.

When purified water was added to the resulting dry syrup at a concentration of compound 1 of 49.4 mg/mL (40.0 mg (potency)/mL), the dry syrup rapidly dissolved in it to give a clear orange solution.

Preparation example 2 of dry syrup

| Ingredients | Weight: mg/g |
|---|---|
| Compound 1 | 123.5 |
| Sucrose | 563.75 |
| D-mannitol | 290.0 |
| Saccharin sodium | 1.25 |
| Hydroxypropylcellulose | 20.0 |
| Colorant Yellow No. 5 | 0.5 |
| Disodium ethylenediaminetetraacetate | 1.0 |
| Orange essence | trace |

A dry syrup having the composition above was prepared as follows. Compound 1, sucrose, D-mannitol, saccharin sodium and disodium ethylenediaminetetraacetate were mixed in an agitating granulator. This mixture was granulated by agitation while spraying it with a binder of hydroxypropylcellulose and Yellow No. 5 in water. These granules were granulated by extrusion through a 42-mesh screen in an extrusion granulator. The granules were dried in a fluidized bed granulator and then sprayed with orange essence. The granules were further dried in the same apparatus and then removed and screened through a 30-mesh sieve to give a desired dry syrup.

When purified water was added to the resulting dry syrup at a concentration of compound 1 of 49.4 mg/mL, the dry syrup rapidly dissolved in it to give a clear orange solution.

Preparation example 3 of dry syrup

| Ingredients | Weight: mg/g |
|---|---|
| Compound 1 | 123.5 |
| Sucrose | 557.5 |
| D-mannitol | 297.5 |
| Hydroxypropylcellulose | 20.0 |
| Colorant Yellow No. 5 | 0.5 |
| Disodium calcium ethylenediaminetetraacetate | 1.0 |
| Orange essence | trace |

A dry syrup having the composition above was prepared as follows. Compound 1, sucrose, D-mannitol and disodium calcium ethylenediaminetetraacetate were mixed in a V model mixer. Separately, hydroxypropylcellulose and Yellow No. 5 were dissolved in water to prepare a binder. The mixed powder was granulated while spraying it with the binder in a fluidized bed granulator. The granules were sprayed with orange essence and then dried in the same apparatus. The granules were removed and screened through a 30-mesh sieve to give a desired dry syrup.

When purified water was added to the resulting dry syrup at a concentration of compound 1 of 49.4 mg/mL, the dry syrup rapidly dissolved in it to give a clear orange solution. After the solution was stored at 10° C. for 6 days, no change in appearance was observed and the residual retention to the initial potency was 98.3%, showing good stability attributed to the effect of disodium calcium ethylenediaminetetraacetate.

What is claimed is:

1. An oral antibacterial composition formulated as a dry syrup comprising faropenem or a salt thereof, or a solvate of either entity as an active ingredient, and an α,ω-diamineacetate compound as an agent for stabilizing the active ingredient, in an amount about 1–100% (w/w) relative to the active ingredient.

2. The composition of claim 1 wherein the α,ω-diamineacetate compound is selected from the group consisting of ethylenediaminetetraacetic acid, hydroxyethylethylenediaminetriacetic acid, dihydroxyethylethylenediaminediacetic acid, 1,3-propanediaminetetraacetic acid, diethylenetriaminepentaacetic acid, triethylenetetraminehexaacetic acid and salts thereof.

3. The composition of claim 2 wherein the α,ω-diamineacetate compound is ethylenediaminetetraacetic acid or a salt thereof.

4. The composition of any one of claim 1, 2 or 3 wherein the active ingredient is faropenem sodium.

5. The composition of claim 4 which is prepared via a state in which the active ingredient is in contact with water.

6. The composition of claim 4 which is in a solid state and is dissolved or suspended in water before being taken orally.

7. The composition of claim 4, wherein said dry syrup forms a clear solution when water is added to said dry syrup.

8. The composition of claim 7, which forms a clear solution containing faropenem sodium at least at 49.4 mg/mL when water is added.

* * * * *